(12) United States Patent
Hirai et al.

(10) Patent No.: US 12,225,173 B2
(45) Date of Patent: Feb. 11, 2025

(54) TELEMEDICINE SYSTEM, TELEMEDICINE METHOD, INFORMATION PROCESSING DEVICE, AND PROGRAM

(71) Applicant: SONY GROUP CORPORATION, Tokyo (JP)

(72) Inventors: Takayoshi Hirai, Tokyo (JP); Yohei Ebihara, Tokyo (JP); Naoto Nakamura, Tokyo (JP); Hironori Suzuki, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 169 days.

(21) Appl. No.: 17/905,523

(22) PCT Filed: Feb. 26, 2021

(86) PCT No.: PCT/JP2021/007356
§ 371 (c)(1),
(2) Date: Sep. 2, 2022

(87) PCT Pub. No.: WO2021/182129
PCT Pub. Date: Sep. 16, 2021

(65) Prior Publication Data
US 2023/0129028 A1 Apr. 27, 2023

(30) Foreign Application Priority Data
Mar. 12, 2020 (JP) .................... 2020-042829

(51) Int. Cl.
*H04N 1/60* (2006.01)
*G16H 80/00* (2018.01)
(Continued)

(52) U.S. Cl.
CPC .......... *H04N 1/6027* (2013.01); *G16H 80/00* (2018.01); *H04N 7/142* (2013.01); *H04N 13/30* (2018.05); *H04N 23/71* (2023.01); *H04N 23/88* (2023.01)

(58) Field of Classification Search
CPC ...... H04N 1/6027; H04N 13/30; H04N 23/88; H04N 23/71; H04N 7/142; H04N 1/60; G16H 80/00
See application file for complete search history.

(56) References Cited

U.S. PATENT DOCUMENTS

| 6,856,354 B1* | 2/2005 | Ohsawa | H04N 23/88 348/370 |
| 2022/0240779 A1* | 8/2022 | Peyman | A61B 5/1176 |
| 2024/0321435 A1* | 9/2024 | Mizobe | G16H 30/40 |

FOREIGN PATENT DOCUMENTS

| JP | 2001-258044 A | 9/2001 |
| JP | 2018-122110 A | 8/2018 |
| JP | 2020-027409 A | 2/2020 |

OTHER PUBLICATIONS

International Search Report and Written Opinion of PCT Application No. PCT/JP2021/007356, issued on May 25, 2021, 09 pages of ISRWO.

* cited by examiner

*Primary Examiner* — Olisa Anwah
(74) *Attorney, Agent, or Firm* — CHIP LAW GROUP (57) ABSTRACT

The present technique relates to a telemedicine system, a telemedicine method, an information processing device, and a program that allow a medical practitioner to more accurately obtain visual information on a patient in telemedicine. The telemedicine system includes a first imaging unit that images a patient in a first space, an image processing unit that corrects an image of the patient based on imaging
(Continued)

conditions in a first space and display conditions in a second space for displaying the image of the patient imaged in the first space, and a display unit that displays the corrected image of the patient in the second space. The present technique can be applied to, for example, a telemedicine system.

18 Claims, 8 Drawing Sheets

(51) Int. Cl.
    *H04N 7/14*     (2006.01)
    *H04N 13/30*     (2018.01)
    *H04N 23/71*     (2023.01)
    *H04N 23/88*     (2023.01)

TELEMEDICINE SYSTEM, TELEMEDICINE METHOD, INFORMATION PROCESSING DEVICE, AND PROGRAM

CROSS REFERENCE TO RELATED APPLICATIONS

This application is a U.S. National Phase of International Patent Application No. PCT/JP2021/007356 filed on Feb. 26, 2021, which claims priority benefit of Japanese Patent Application No. JP 2020-042829 filed in the Japan Patent Office on Mar. 12, 2020. Each of the above-referenced applications is hereby incorporated herein by reference in its entirety.

TECHNICAL FIELD

The present technique relates to a telemedicine system, a telemedicine method, an information processing device, and a program and particularly relates to a telemedicine system, a telemedicine method, an information processing device, and a program that allow a medical practitioner to more accurately obtain visual information on a patient in telemedicine.

BACKGROUND ART

Conventionally, telemedicine is proposed such that a patient can undergo medical care (e.g., an examination, a diagnosis, or treatment) provided by a medical practitioner from a remote location (e.g., see PTL 1). For example, telemedicine shortens the waiting time of a patient and allows a patient who has difficulty in going to the hospital because of aging or the like to easily undergo medical care provided by a medical practitioner.

CITATION LIST

Patent Literature

[PTL 1]
JP 2018-122110 A

SUMMARY

Technical Problem

In telemedicine, however, a medical practitioner observes a patient through a monitor, so that visual information on the patient may be different from information obtained by face-to-face medical care, the visual information being obtained by observing the patient by the medical practitioner. In other words, in telemedicine, the medical practitioner may incorrectly obtain visual information on the patient.

The present technique has been made in view of such a situation and allows a medical practitioner to more accurately obtain visual information on a patient in telemedicine.

Solution to Problem

A telemedicine system according to a first aspect of the present technique includes a first imaging unit that images a patient in a first space, an image processing unit that corrects an image of the patient based on imaging conditions in a first space and display conditions in a second space for displaying the image of the patient imaged in the first space, and a display unit that displays the corrected image of the patient in the second space.

A telemedicine method according to the first aspect of the present technique includes: imaging a patient in a first space; correcting an image of the patient based on imaging conditions in the first space and display conditions in a second space for displaying the image of the patient imaged in the first space; and displaying the corrected image of the patient in the second space.

An information processing device according to a second aspect of the present technique includes an image processing unit that corrects an image of a patient based on imaging conditions for imaging the patient in a first space and display conditions in a second space for displaying the image of the patient imaged in the first space.

A program according to the second aspect of the present technique causes a computer to perform processing of correcting an image of a patient based on imaging conditions for imaging the patient in a first space and display conditions in a second space for displaying the image of the patient imaged in the first space.

In the first aspect of the present technique, the patient is imaged in the first space; an image of the patient is corrected based on the imaging conditions in the first space and the display conditions in the second space for displaying the image of the patient imaged in the first space; and the corrected image of the patient is displayed in the second space.

In the second aspect of the present technique, an image of a patient is corrected based on the imaging conditions for imaging the patient in the first space and the display conditions in the second space for displaying the image of the patient imaged in the first space.

DESCRIPTION OF EMBODIMENTS

An embodiment for implementing the present technique will be described below. The description will be made in the following order.
1. Background
2. Embodiment
3. Modification Examples
4. Others

1. Background

In conventional face-to-face medical care, a medical practitioner provides medical care for a patient in person in the same space (e.g., in a consultation room) under the same environment. Thus, a medical practitioner deliberately or unconsciously compares a skin color or the like of a patient with that in the experience of the medical practitioner or a scene in the field of view and uses the comparison to determine the presence or absence of a disease.

In this case, a medical practitioner is a person who provides medical care and conducts diagnosis and treatment on a patient, and is not limited to a doctor. For example, medical practitioners include a nurse, a pharmacist, a dentist, and a hygienist. A patient is a person who undergoes medical care by a medical practitioner regardless of whether the person is suffering from a disease.

In contrast, in telemedicine, a patient and a medical practitioner are present in different spaces, so that an environment where the patient is imaged is different from an environment where the image of the patient (hereinafter referred to as a patient image) is examined by the medical practitioner. Thus, visual information obtained for the patient (hereinafter referred to as patient visual information) by the medical practitioner may be different from that in face-to-face medical care, leading to unexpected wrong diagnosis.

For example, if a patient is illuminated with yellow light while a medical practitioner is illuminated with blue light, the medical practitioner is more likely to be affected by an impression of yellow components in a patient image unlike in the case where the medical practitioner is present with the patient in the same space. Hence, the medical practitioner is more likely to erroneously diagnose the patient as jaundice or the like.

Moreover, depending upon the conditions of a camera for imaging a patient, a display device for displaying a patient image, and equipment including a transmission line for transmitting a patient image, a difference increases between patient visual information obtained by a medical practitioner in telemedicine and patient visual information obtained by a medical practitioner in face-to-face medical care.

The difference in patient visual information depending upon the conditions of equipment is multiplied though each part of the equipment. The multiplied difference is, for example, a color variation in a patient image because of the type, the manufacturing error, and the setting or the like of a camera, a color change made in a patient image by compression and decompression during transmission, or a color variation in a patient image because of the type, the manufacturing error, and the setting or the like of a display device. This further increases a difference between patient visual information obtained by a medical practitioner in telemedicine and patient visual information obtained by a medical practitioner in face-to-face medical care.

Furthermore, the conditions of equipment vary among patients or examinations and thus are hard to adjust with uniformity.

As described above, telemedicine may cause a difference from patient visual information obtained by face-to-face medical care, thereby preventing a medical practitioner from accurately acquiring patient visual information.

In contrast, the present technique is devised to reduce a difference from patient visual information obtained by face-to-face medical care, allowing a medical practitioner to accurately obtain patient visual information in telemedicine.

2. Embodiment

Referring to FIGS. 1 to 8, an embodiment of the present technique will be described below.

Configuration Example of Telemedicine System 1

Figure 1:
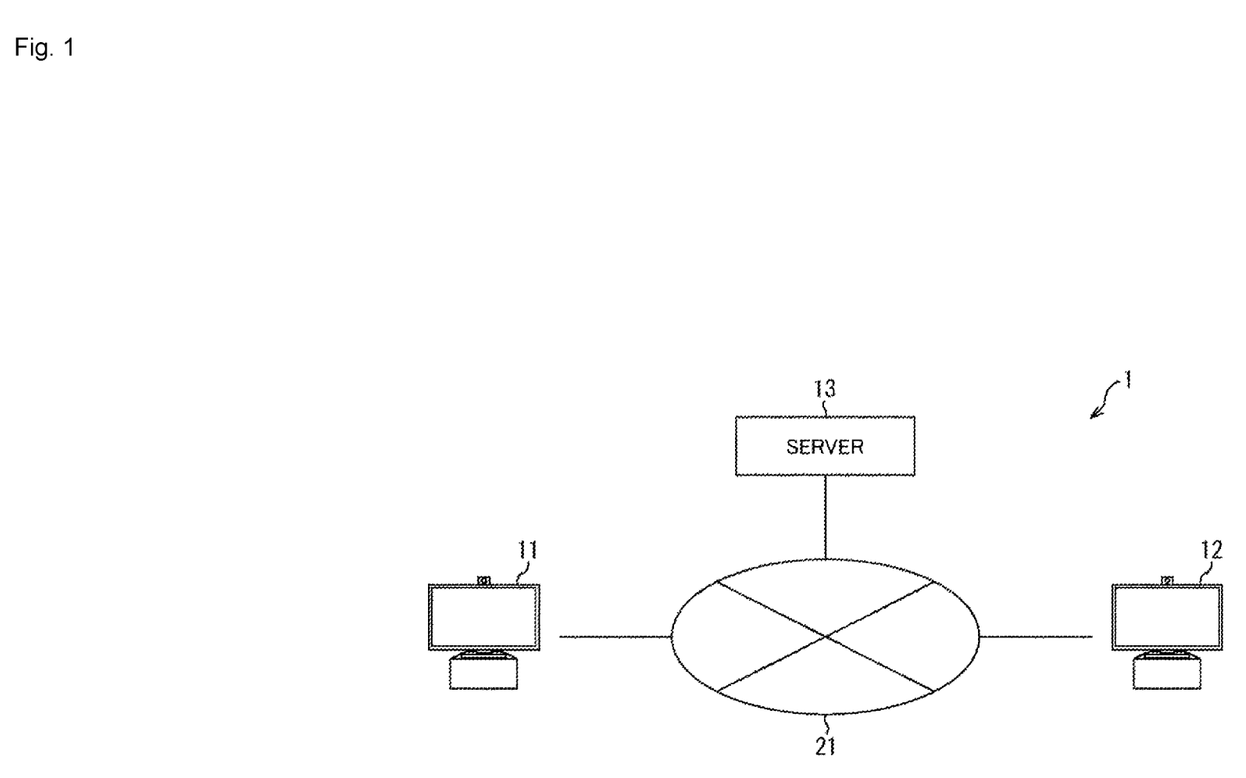
FIG. 1 is a block diagram illustrating an embodiment of a telemedicine system to which the present technique is applied.

FIG. 1 illustrates an embodiment of a telemedicine system 1 to which the present technique is applied.

The telemedicine system 1 includes a patient terminal 11, a medical practitioner terminal 12, and a server 13. The patient terminal 11, the medical practitioner terminal 12, and the server 13 are connected to one another via a network 21.

In the telemedicine system 1, the patient terminal 11 and the medical practitioner terminal 12 communicate with each other and transfer various kinds of data to each other via the server 13, achieving telemedicine.

The patient terminal 11 is an information processing device that is used by a patient and includes, for example, a computer, a TV, or a smartphone. The patient terminal 11 is disposed in a space where a patient undergoes telemedicine (hereinafter referred to as a patient space). The patient space is not particularly limited. For example, the space may be a room of a patient's house, a patient's room in a lodging facility, a store, various facilities, a vehicle, or an outdoor space.

The medical practitioner terminal 12 is an information processing device that is used by a medical practitioner and includes, for example, a computer. The medical practitioner terminal 12 is disposed in a space that is different from the patient space and is provided for telemedicine conducted by a medical practitioner (hereinafter referred to as a medical practitioner space). The medical practitioner space is not particularly limited. For example, the space may be a consultation room of a medical institution or a room in the house of a medical practitioner.

The server 13 is an information processing device to which client terminals (e.g., the patient terminal 11 and the medical practitioner terminal 12) are connectable. The server 13 includes, for example, a computer.

The server 13 transmits data from one of the client terminals to the other client terminal and optionally performs a variety of processing on data. For example, the server 13 receives image data corresponding to a patient image from the patient terminal 11, corrects the patient image, and transmits image data corresponding to the corrected patient image to the medical practitioner terminal 12.

In this way, the patient terminal 11 and the medical practitioner terminal 12 do not directly communicate with each other but indirectly communicate with each other via the server 13. This can prevent personal information and medical information on patients from being accidentally left at the patient terminal 11 or the medical practitioner terminal 12.

Configuration Example of the Patient Terminal 11

Figure 2:
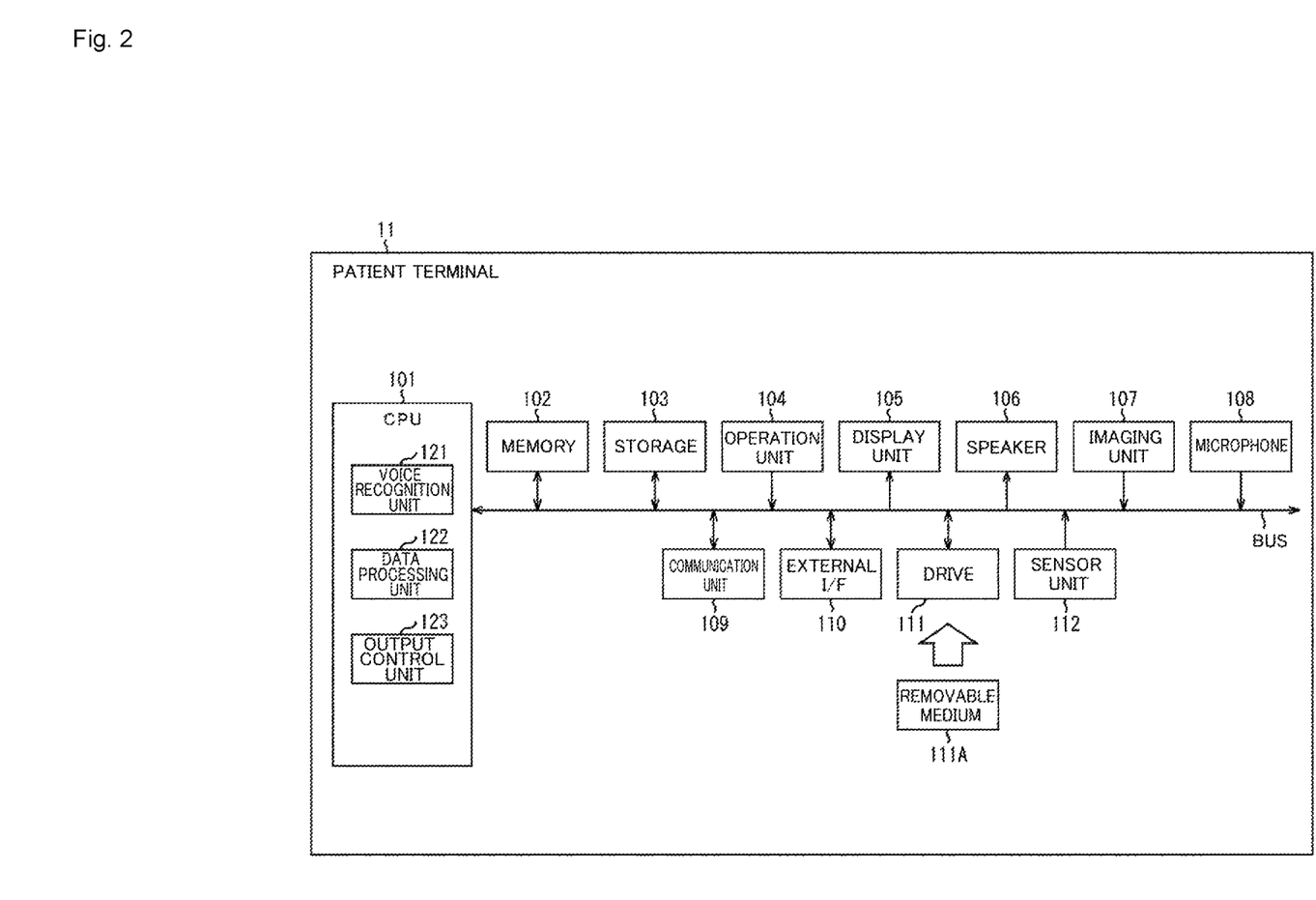
FIG. 2 is a block diagram illustrating a functional configuration example of a patient terminal.
Figure 3:
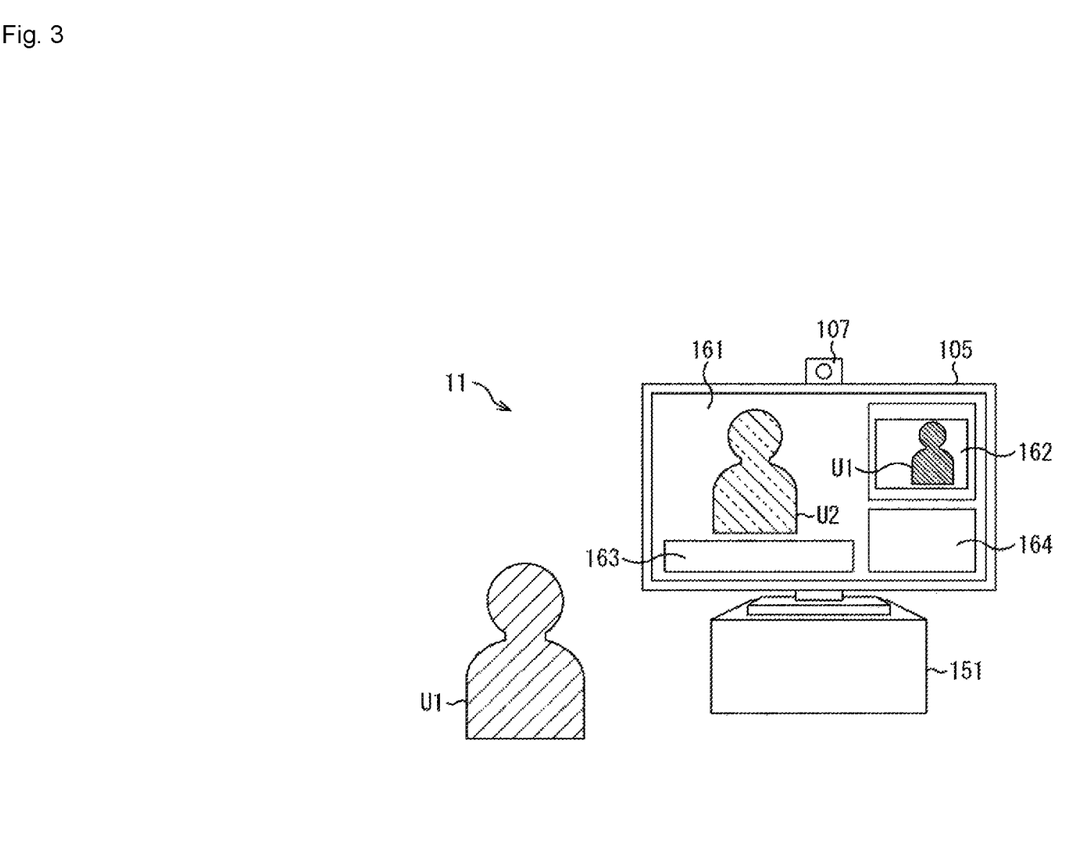
FIG. 3 is a diagram illustrating a configuration example of the appearance of the patient terminal and an example of the display layout of a display unit.
Figure 4:
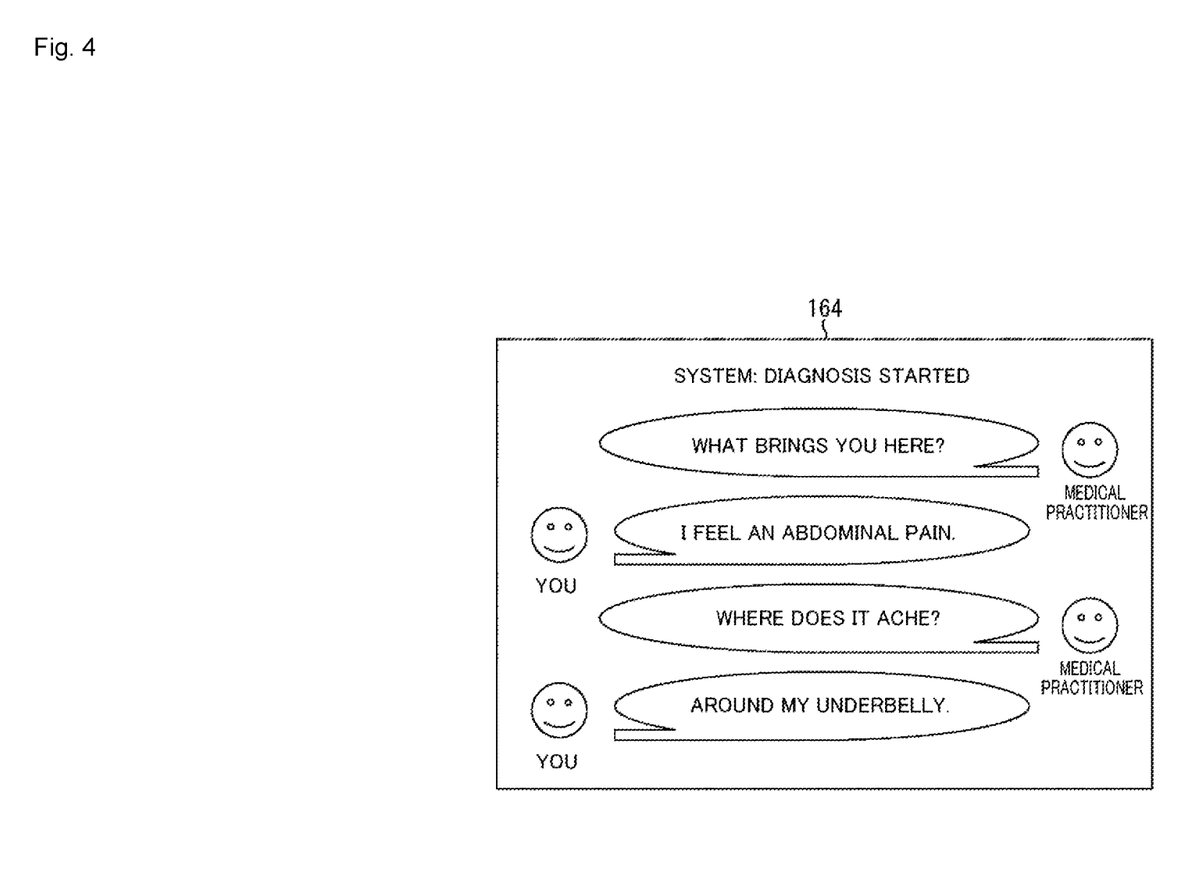
FIG. 4 is a diagram illustrating an example of an action log.

Referring to FIGS. 2 to 4, a configuration example of the patient terminal 11 will be described below.

FIG. 2 is a block diagram illustrating a functional configuration example of the patient terminal 11.

The patient terminal 11 includes a CPU (Central Processing Unit) 101, a memory 102, a storage 103, an operation unit 104, a display unit 105, a speaker 106, an imaging unit 107, a microphone 108, a communication unit 109, an external I/F 110, a drive 111, and a sensor unit 112. The units from the CPU 101 to the sensor unit 112 are connected to a bus and conduct necessary communications with one another.

The CPU 101 performs a variety of processing by running programs installed in the memory 102 and the storage 103.

The memory 102 includes, for example, a volatile memory and temporarily stores the program to be executed by the CPU 101 and necessary data.

The storage 103 includes, for example, a hard disk or a nonvolatile memory and stores the program to be executed by the CPU 101 and necessary data.

The operation unit 104 includes a physical key (including a key board), a mouse, and a touch panel. The operation unit 104 outputs an operation signal onto the bus in response to a user operation, the operation signal corresponding to the user operation.

The display unit 105 includes, for example, a display device such as an LCD (Liquid Crystal Display) and displays an image according to data supplied from the bus.

In this configuration, a touch panel acting as the operation unit 104 includes a transparent member and can be integrated with the display unit 105. Thus, a user (e.g., a patient) can input information so as to operate an icon or a button that is displayed on the display unit 105.

The speaker 106 outputs sound according to data supplied from the bus.

The imaging unit 107 includes, for example, a digital camera. The imaging unit 107 captures (senses light) an image (a still image or a moving image) and outputs corresponding image data onto the bus.

The microphone 108 collects sounds (senses sounds) and outputs corresponding sound data onto the bus.

The communication unit 109 includes a communication circuit and an antenna and communicates with the server 13 or the like via the network 21.

The external I/F (interface) 110 is an interface for exchanging data with various external devices.

In the drive 111, for example, a removable medium 111A such as a memory card can be loaded and removed. The drive 111 drives the loaded removable medium 111A.

The sensor unit 112 includes a sensor other than the imaging unit 107 for sensing light and the microphone 108 for sensing sound, that is, a sensor for sensing a different physical quantity different from those of the imaging unit 107 and the microphone 108. The sensor unit 112 senses any physical quantity or any kind of physical quantity. For example, physical quantities such as a temperature, a humidity, and illuminance, an acceleration, an angular velocity, and geomagnetism may be sensed. The sensor unit 112 outputs sensor data, which indicates the sensed physical quantity, onto the bus.

In the patient terminal 11 configured thus, the program (e.g., a patient application) to be executed by the CPU 101 can be recorded in advance in the storage 103 serving as a recording medium contained in the CPU 101.

The program is provided as so-called package software that is stored (recorded) in the removable medium 111A. The program can be installed on the patient terminal 11 from the removable medium 111A.

Additionally, the program can be downloaded from the server 13 or the like via the network 21 and the communication unit 109 and can be installed on the patient terminal 11.

The CPU 101 can act as a voice recognition unit 121, a data processing unit 122, and an output control unit 123 by running the program installed on the patient terminal 11.

The voice recognition unit 121 performs voice recognition on, for example, on voice data outputted from the microphone 108 and outputs voice recognition data, which indicates the result of the voice recognition, onto the bus.

The data processing unit 122 performs processing on various kinds of data used for the processing of telemedicine. For example, the data processing unit 122 generates imaging condition data that indicates the conditions for imaging a patient. For example, the data processing unit 122 generates input data that indicates contents inputted by a user (e.g., a patient), based on an operation signal from the operation unit 104. For example, the data processing unit 122 optionally performs a variety of processing on transmission data to be transmitted to the medical practitioner terminal 12. The transmission data includes, for example, image data, voice data, voice recognition data, sensor data, imaging condition data, and input data. For example, the data processing unit 122 optionally performs a variety of processing on data acquired from the medical practitioner terminal 12.

The output control unit 123 controls, for example, the display of an image by the display unit 105 and the output of sound from the speaker 106.

FIG. 3 illustrates a configuration example of the appearance of the patient terminal 11 and an example of the display layout of the display unit 105.

In this example, the display unit 105 is mounted on a main unit 151, and the imaging unit 107 is mounted on the display unit 105. The main unit 151 contains, for example, the CPU 101, the memory 102, the storage 103, the communication unit 109, the external I/F 110, the drive 111, and the sensor unit 112 that are illustrated in FIG. 2.

The screen of the display unit 105 is divided into, for example, display areas 161 to 164.

In the display area 161, an image of a medical practitioner U2 is displayed, the image being captured by the medical practitioner terminal 12.

In the display area 162, an image of a patient U1 is displayed, the image being captured by the imaging unit 107.

In the display area 163, for example, a text indicating the voice of the medical practitioner U2 or an option to be selected by the patient U1 is displayed. The voice of the medical practitioner U2 is recognized by the medical practitioner terminal 12, and the option is inputted to the medical practitioner terminal 12 by the medical practitioner U2.

In the display area 164, an action record log by the patient U1 or the medical practitioner U2 is displayed. The action record log includes, for example, the comments of the patient U1 and the medical practitioner U2 and information or the like selected or inputted by the patient U1 and the medical practitioner U2.

FIG. 4 illustrates an example of the action record log. In this example, a patient icon is displayed on the left side of the display area 164 while a medical practitioner icon is displayed on the right side. The comments of the patient U1 or the medical practitioner U2 and information or the like selected or inputted by the patient U1 and the medical practitioner U2 are displayed in time sequence while being associated with the icons.

For example, the patient U1 is diagnosed by the medical practitioner U2 displayed on the display unit 105. For example, the patient U1 can undergo medical care by the medical practitioner U2 via telemedicine by answering a question from the medical practitioner U2 displayed on the display unit 105 or selecting an option displayed in the display area 163.

Configuration Example of Medical Practitioner Terminal 12

Figure 5:
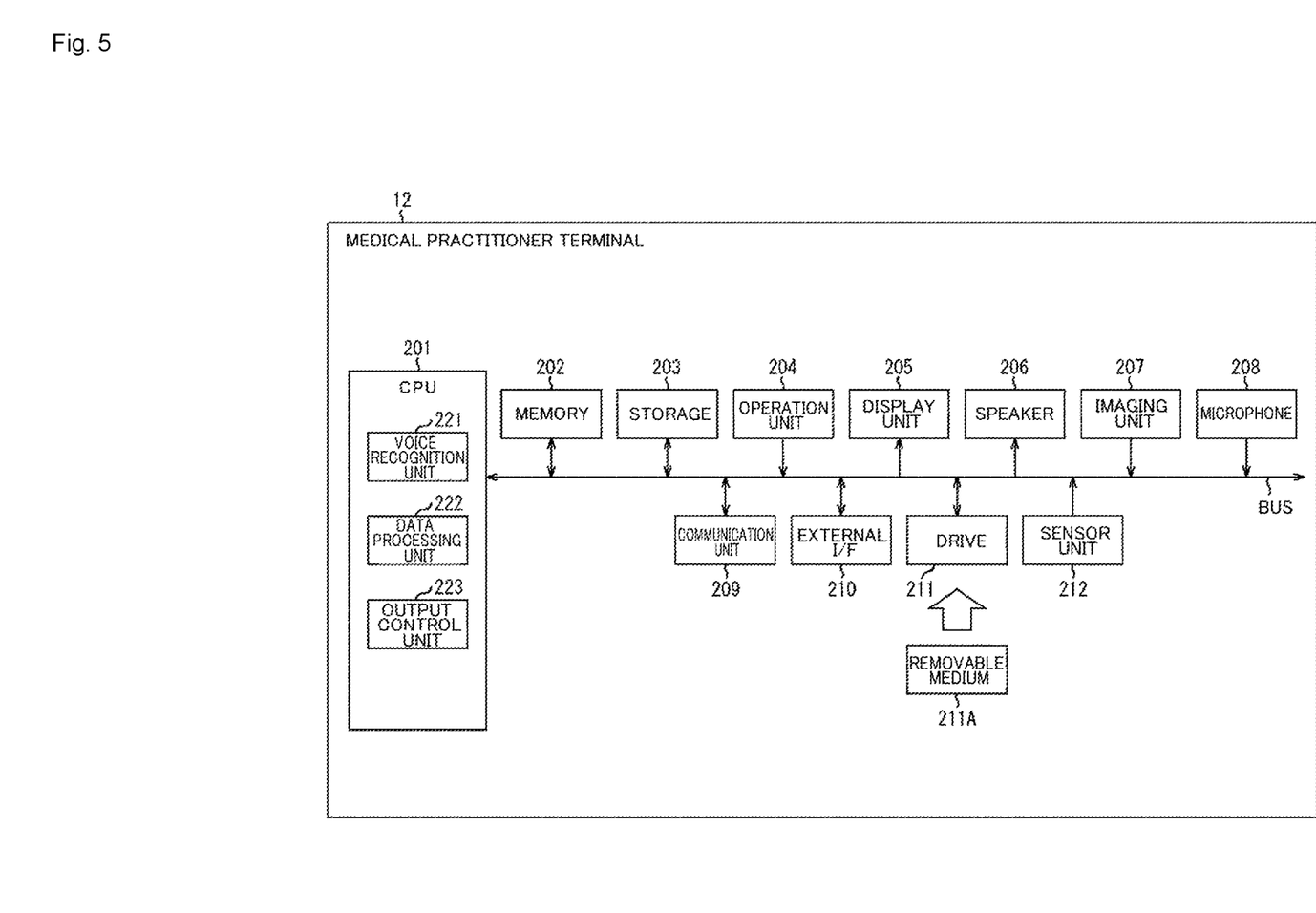
FIG. 5 is a block diagram illustrating a functional configuration example of a medical practitioner terminal.
Figure 6:
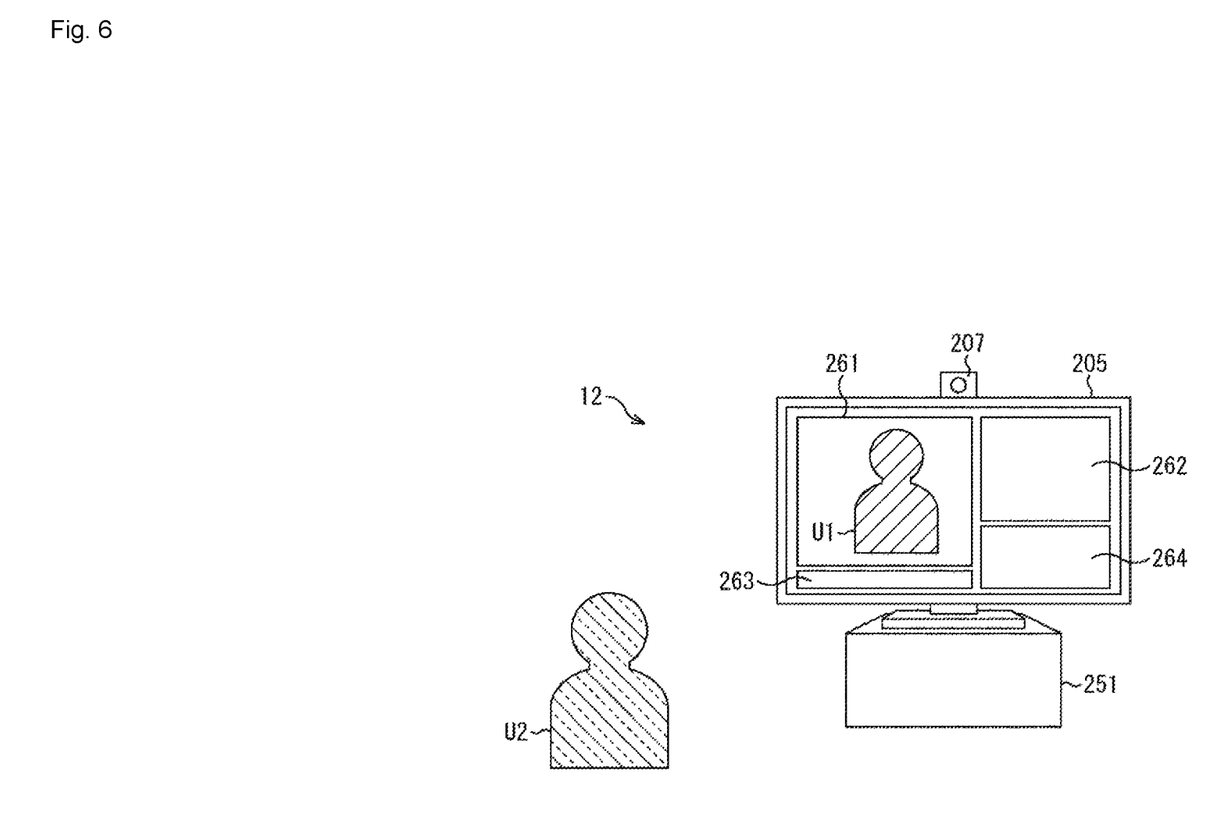
FIG. 6 is a diagram illustrating a configuration example of the appearance of the medical practitioner terminal and an example of the display layout of the display unit.

Referring to FIGS. 5 and 6, a configuration example of the medical practitioner terminal 12 will be described below.

FIG. 5 is a block diagram illustrating a functional configuration example of the medical practitioner terminal 12.

The medical practitioner terminal 12 includes a CPU 201, a memory 202, a storage 203, an operation unit 204, a display unit 205, a speaker 206, an imaging unit 207, a microphone 208, a communication unit 209, an external I/F 210, a drive 211, and a sensor unit 212. The units from the CPU 201 to the sensor unit 212 are connected to a bus and conduct necessary communications with one another.

The configurations of the CPU 201 to the sensor unit 212 are similar to those of the CPU 101 to the sensor unit 112 in FIG. 2.

In the medical practitioner terminal 12, as in the patient terminal 11, a program (e.g., a medical practitioner application) to be executed by the CPU 201 can be recorded in advance in the storage 203 serving as a recording medium contained in the medical practitioner terminal 12.

The program is provided as package software that is stored (recorded) in a removable medium 211A. The program can be installed on the medical practitioner terminal 12 from the removable medium 211A.

Additionally, the program can be downloaded from the server 13 or the like via the network 21 and the communication unit 209 and can be installed on the medical practitioner terminal 12.

The CPU 201 can act as a voice recognition unit 221, a data processing unit 222, and an output control unit 223 by running the program installed on the medical practitioner terminal 12.

The voice recognition unit 221 performs voice recognition on, for example, on voice data collected by the microphone 208 and outputs voice recognition data, which indicates the result of the voice recognition, onto the bus.

The data processing unit 222 performs processing on various kinds of data used for the processing of telemedicine. For example, the data processing unit 222 generates display condition data that indicates the conditions for displaying a patient image. For example, the data processing unit 222 generates input data that indicates contents inputted by a user (e.g., a medical practitioner), based on an operation signal from the operation unit 204. For example, the data processing unit 222 optionally performs a variety of processing on transmission data to be transmitted to the patient terminal 11. The transmission data includes, for example, image data, voice data, voice recognition data, sensor data, display condition data, and input data. For example, the data processing unit 222 optionally performs a variety of processing on data acquired from the patient terminal 11.

The output control unit 223 controls, for example, the display of an image by the display unit 205 and the output of sound from the speaker 206.

FIG. 6 illustrates a configuration example of the appearance of the medical practitioner terminal 12 and an example of the display layout of the display unit 205.

In this example, the display unit 205 is mounted on a main unit 251, and the imaging unit 207 is mounted on the display unit 205. The main unit 251 contains, for example, the CPU 201, the memory 202, the storage 203, the communication unit 209, the external I/F 210, the drive 211, and the sensor unit 212 that are illustrated in FIG. 5.

The screen of the display unit 205 is divided into, for example, display areas 261 to 264.

In the display area 261, an image of the patient U1 is displayed, the image being captured by the patient terminal 11.

In the display area 262, for example, the electronic medical chart of the patient U1 is displayed.

In the display area 263, for example, a text indicating the voice of the patient U1, a question to the patient U1, or an answer to the question is displayed. The voice of the patient U1 is recognized by the patient terminal 11, the question is inputted by the medical practitioner U2, and the answer is inputted to the patient terminal 11 by the patient U1. The question to the patient U1 includes, for example, a plurality of options.

In the display area 264, for example, an action record log is displayed as in the display area 164 of the patient terminal 11 in FIG. 3.

For example, the medical practitioner U2 can perform telemedicine on the patient U1 by asking a question to the patient U1 displayed on the display unit 205, referring to information on symptoms presented by the patient U1, or visually checking an image of the patient U1.

Configuration Example of Server 13

Figure 7:
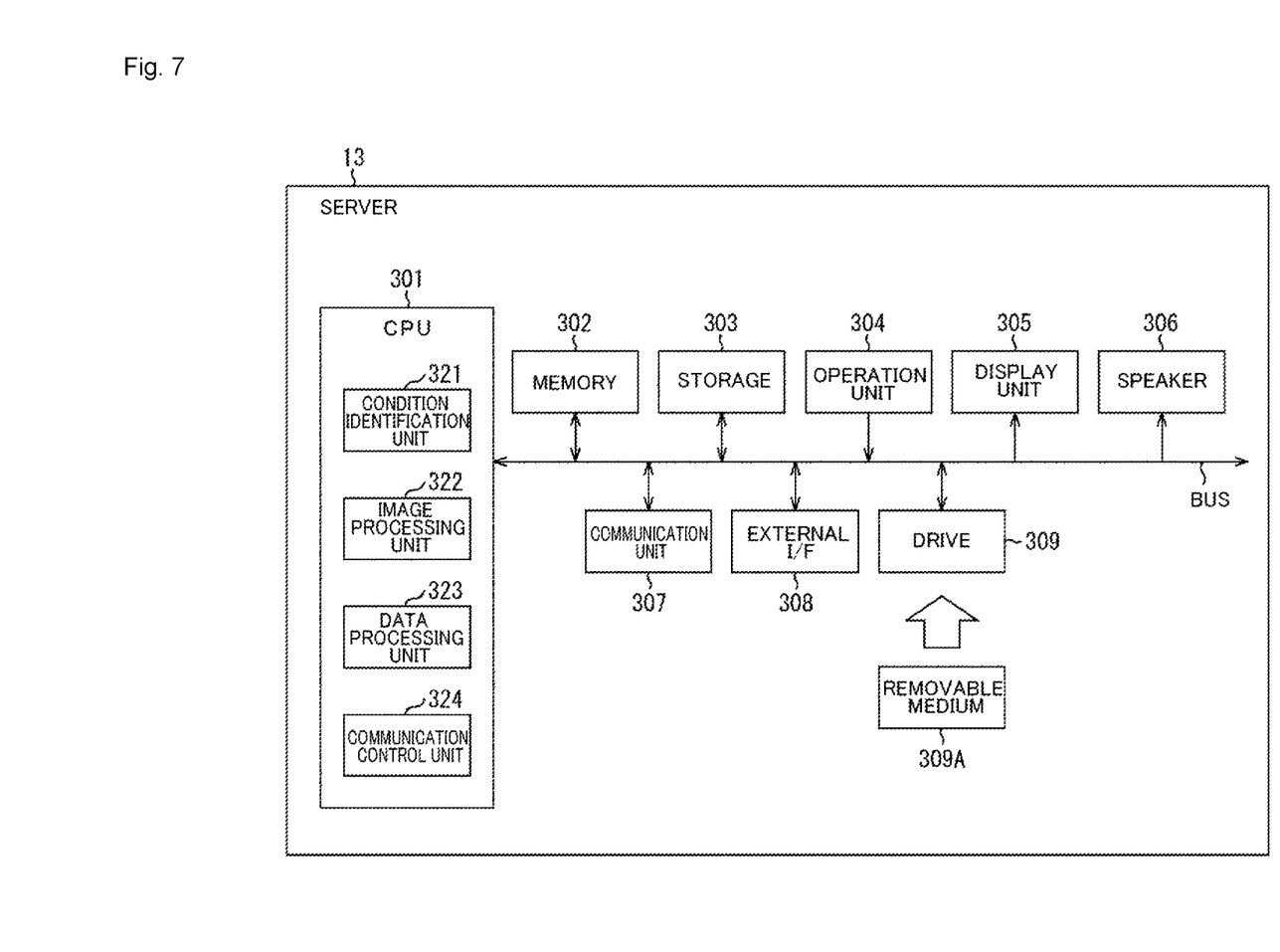
FIG. 7 is a block diagram illustrating a functional configuration example of a server.

FIG. 7 is a block diagram illustrating a functional configuration example of the server 13.

The server 13 includes a CPU 301, a memory 302, a storage 303, an operation unit 304, a display unit 305, a speaker 306, a communication unit 307, an external I/F 308, and a drive 309. The units from the CPU 301 to the drive 309 are connected to a bus and conduct necessary communications with one another.

The configurations of the CPU 301 to the drive 309 are similar to those of the CPU 101 to the speaker 106 and the communication unit 109 to the drive 111 in FIG. 2.

In the server 13, as in the patient terminal 11, a program to be executed by the CPU 301 can be recorded in advance in the storage 303 serving as a recording medium contained in the server 13.

The program is provided as package software that is stored (recorded) in a removable medium 309A. The program can be installed on the server 13 from the removable medium 309A.

Additionally, the program can be downloaded from another server (not illustrated) via the network 21 and the communication unit 307 and can be installed on the server 13.

The CPU 301 can act as a condition identification unit 321, an image processing unit 322, a data processing unit 323, and a communication control unit 324 by running the program installed on the server 13.

The condition identification unit 321 identifies the imaging conditions for imaging a patient on the patient terminal 11, based on imaging condition data acquired from the patient terminal 11. Furthermore, the condition identification unit 321 identifies the display conditions for displaying a patient image on the medical practitioner terminal 12, based on display condition data acquired from the medical practitioner terminal 12.

The image processing unit 322 corrects a patient image corresponding to image data acquired from the patient terminal 11, based on the imaging conditions of a patient and the display conditions of a patient image. The image processing unit 322 outputs, onto the bus, image data corresponding to the corrected patient image.

For example, the data processing unit 323 optionally performs a variety of processing on data other than image data corresponding to a patient image from among data transferred between the patient terminal 11 and the medical practitioner terminal 12. The data processing unit 323 generates an action record log based on, for example, the data transferred between the patient terminal 11 and the medical practitioner terminal 12.

The communication control unit 324 controls communications between the patient terminal 11 and the medical practitioner terminal 12. For example, the communication control unit 324 controls the transmission of various kinds of data to the medical practitioner terminal 12 after the data is received from the patient terminal 11. For example, the communication control unit 324 controls the transmission of various kinds of data to the patient terminal 11 after the data is received from the medical practitioner terminal 12.

<Patient Image Correction>

Figure 8:
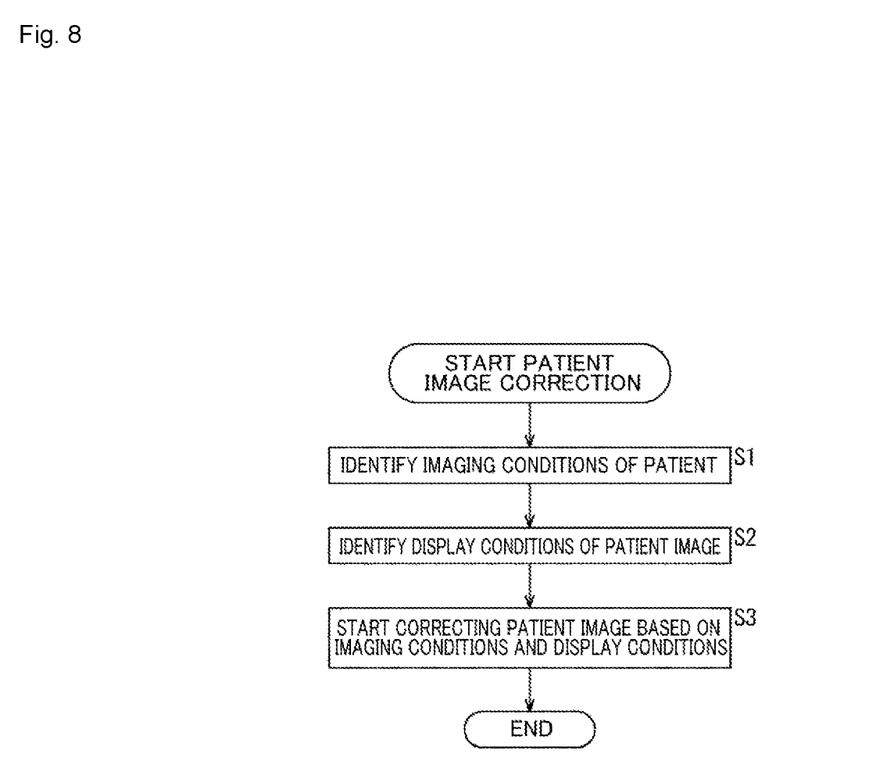
FIG. 8 is a flowchart for explaining the correction of a patient image.

Referring to FIG. 8, the correction of a patient image by the server 13 will be described below.

This processing is started, for example, when telemedicine is started or at least the imaging conditions of a patient in a patient space or the display conditions of a patient image in a medical practitioner space are changed.

In step S1, the condition identification unit 321 identifies the imaging conditions of a patient.

Specifically, the data processing unit 122 of the patient terminal 11 generates imaging condition data on the imaging conditions of the patient and transmits the data to the server 13 via the communication unit 109.

The imaging condition data includes, for example, image data corresponding to a patient image of the patient imaged by the imaging unit 107. For example, if the sensor unit 112 of the patient terminal 11 includes a thermometer and an illuminometer or the like, the imaging condition data may include the measurement results of a temperature and an illuminance or the like in a patient space.

In response to the transmission, the condition identification unit 321 receives the imaging condition data via the network 21 and the communication unit 307 and identifies the imaging conditions of the patient based on the imaging condition data.

For example, the condition identification unit 321 identifies the illumination conditions of a patient space as the imaging conditions of the patient. For example, the condition identification unit 321 identifies, as the illumination conditions of the patient space, the conditions of at least one of the color (e.g., hue, saturation, or lightness) of illumination light, the brightness of illumination light, and the kind of light source.

For example, the condition identification unit 321 identifies the illumination conditions of the patient space by using a predetermined function. Specifically, for example, the condition identification unit 321 extracts an area where the skin of the patient is exposed (hereinafter referred to as a skin area), from the patient image. The condition identification unit 321 calculates tristimulus values (CIE-XYZ) from the pixel values (RGB values) of the skin area of the patient image according to a sensor correlational method. The condition identification unit 321 identifies color temperatures corresponding to the calculated tristimulus values, as the color temperatures of the light source in the patient space by using a predetermined translation table. In other words, the condition identification unit 321 identifies the color temperatures of the light source in the patient space on the assumption that the spectral distribution of the light source in the patient space agrees with the spectral distribution of blackbody radiation.

The translation table is a table indicating a correspondence between the tristimulus values and the color temperatures. The table is recorded in advance in the storage 303.

Alternatively, for example, the condition identification unit 321 identifies the illumination conditions of the patient space by using machine learning.

Specifically, pieces of learning data are prepared such that an image of a person is labeled with the illumination conditions of a space where the image is captured. Furthermore, by using the learning data and any machine learning algorithm of deep learning or the like, a classifier (estimation algorithm) is generated to estimate, based on the image of the person, the illumination conditions of the space where the image is captured.

The generated classifier is used for the condition identification unit 321. For example, when a patient image is inputted, the condition identification unit 321 outputs the illumination conditions of a patient space based on the inputted patient image.

The illumination light of the patient space is not always limited to artificial light. For example, natural light, e.g., sunlight may be used instead.

In step S2, the condition identification unit 321 identifies the display conditions of the patient image.

Specifically, the data processing unit 222 of the medical practitioner terminal 12 generates display condition data on the display conditions of the patient image and transmits the data to the server 13 via the communication unit 209.

The display condition data includes, for example, image data corresponding to a medical practitioner image of a medical practitioner imaged by the imaging unit 207. For example, if the sensor unit 212 of the medical practitioner terminal 12 includes a thermometer and an illuminometer or the like, the display condition data may include the measurement results of a temperature and an illuminance or the like in a medical practitioner space.

In response to the transmission, the condition identification unit 321 receives the display condition data via the network 21 and the communication unit 307 and identifies the display conditions of the patient image based on the display condition data.

For example, the condition identification unit 321 identifies the illumination conditions of the medical practitioner space as the display conditions of the patient image according to the same method as the illumination conditions of the patient space.

The illumination light of the medical practitioner space is not always limited to artificial light. For example, natural light, e.g., sunlight may be used instead.

In step S3, the image processing unit 322 starts processing for correcting the patient image based on the imaging conditions and the display conditions.

For example, when image data corresponding to a patient image received from the patient terminal 11 is transmitted to the medical practitioner terminal 12, the image processing unit 322 starts processing for correcting the patient image based on a difference between the imaging conditions of the patient and the display conditions of the patient image.

For example, the image processing unit 322 estimates a difference between the illumination conditions of the patient space and the illumination conditions of the medical practitioner space, estimates the view of the patient on the assumption that the patient is present in the medical practitioner space, and corrects the patient image.

Specifically, for example, the image processing unit 322 estimates the skin color of the patient upon changing from the illumination conditions of the patient space to the illumination conditions of the medical practitioner space. The image processing unit 322 then corrects the patient image with reference to the estimated skin color. For example, on the assumption that the skin of the patient is a Lambertian surface, the image processing unit 322 estimates the skin color of the patient in the patient image when the color temperature of the light source is changed from the color temperature of the patient space to the color temperature of the medical practitioner space. The image processing unit 322 corrects the patient image by adjusting a white balance such that the skin of the patient has the estimated color.

Thereafter, the correction of the patient image is terminated.

As described above, by using the corrected patient image, the medical practitioner can observe the patient substantially under the same illumination conditions as the case where the patient is present in the same space. Thus, the medical practitioner can obtain patient visual information as in face-to-face medical care for a patient in the same space, thereby accurately obtaining patient visual information. This can suppress the occurrence of wrong diagnoses in telemedicine.

3. Modification Examples

Hereinafter, modification examples of the foregoing embodiments of the present technique will be described.

Modification Examples of the Correction of a Patient Image

For example, the imaging condition data transmitted from the patient terminal 11 to the server 13 may include the conditions of the configuration and setting of the imaging unit 107. The conditions of the configuration of the imaging unit 107 include, for example, the kinds and models of a camera and a lens that are provided for the imaging unit 107. The conditions of the setting of the imaging unit 107 include, for example, the setting values of exposure conditions such as a shutter speed, an f number, and sensitivity.

Likewise, the display condition data transmitted from the medical practitioner terminal 12 to the server 13 may include the conditions of the configuration and setting of the display unit 205. The conditions of the configuration of the display unit 205 include, for example, the kind and model of a display device provided for the display unit 205. The conditions of the setting of the display unit 205 include, for example, the setting values of display brightness, a color, and a contrast.

The image processing unit 322 of the server 13 then corrects a patient image based on, for example, the configuration and setting of the imaging unit 107 of the patient terminal 11 and the configuration and setting of the display unit 205 of the medical practitioner terminal 12.

For example, a user (e.g., a medical practitioner) may provide an instruction for the server 13 via the medical practitioner terminal 12 so as to set the presence or absence of a correction on a patient image by the image processing unit 322 of the server 13 or the intensity of a correction. Thus, for example, if a medical practitioner determines that a patient image has a large correction error, the correction of the patient image can be canceled.

Moreover, for example, the imaging condition data may include information on a patient to be imaged, and the display condition data may include information on a patient to be displayed. The information on a patient includes, for example, information on at least one of the attribute (e.g., an age, a gender, or a nationality) of the patient and past medical care information (e.g., medical history) on the patient.

Thus, for example, the medical practitioner can set the presence or absence of a correction to the patient image or the intensity of a correction based on the age or the medical history of the patient. For example, if a patient has suffered from a liver disease in the past, a medical practitioner can carefully observe a skin color while switching the presence or absence of a correction to a patient image or the intensity of a correction.

For example, the image processing unit 322 of the server 13 may change the correction contents of a patient image based on the contents of conversation between the patient and the medical practitioner. For example, if a predetermined keyword or phrase is detected in conversation between a patient and a medical practitioner based on the result of voice recognition of the conversation, the image processing unit 322 may change the correction contents of a patient image. For example, if the image processing unit 322 detects a comment from a patient, for example, "a poor skin color," "redness in my skin," or "eczema on my skin," the image processing unit 322 may increase or reduce the intensity of a correction to a patient image. Thus, a medical practitioner can more accurately compare visual information on a patient with the memory of the medical practitioner.

Modification Examples of the Imaging Condition Data and the Display Condition Data For example, a user (e.g., a patient) may enter part or whole of imaging condition data supplied from the patient terminal 11 to the server 13. For example, a patient may enter the model name or installation date of lighting equipment in a patient space into the patient terminal 11.

Likewise, for example, a user (e.g., a medical practitioner) may enter part or whole of display condition data supplied from the medical practitioner terminal 12 to the server 13. For example, a medical practitioner may enter the model name or installation date of lighting equipment in a medical practitioner space into the medical practitioner terminal 12.

The display condition data may include, for example, data on the imaging conditions of a medical practitioner in a medical practitioner space.

For example, if the lighting equipment in the patient space is lighting equipment compliant with IoT (Internet of Things) connectable to the network 21, the condition identification unit 321 of the server 13 may directly acquire data on the illumination conditions from the lighting equipment in the patient space.

Likewise, for example, if the lighting equipment in the medical practitioner space is lighting equipment compliant with IoT connectable to the network 21, the condition identification unit 321 of the server 13 may directly acquire data on the illumination conditions from the lighting equipment in the medical practitioner space.

Modification Example of the Configuration of the Telemedicine System

The configuration and the sharing of processing of the telemedicine system 1 can be modified when necessary.

For example, the processing of the server 13 may be shared between the patient terminal 11 and the medical practitioner terminal 12 without providing the server 13, so that communications may be conducted without the server 13. In this case, for example, the medical practitioner terminal 12 may identify the imaging conditions of a patient and the display conditions of a patient image and correct a patient image. Likewise, for example, the patient terminal 11 may identify the imaging conditions of a patient and the display conditions of a patient image and correct a patient image.

Example of the Patient Terminal 11 Provided with Three-Dimensional Measuring Equipment For example, the patient terminal 11 may be provided with three-dimensional measuring equipment (three-dimensional information detection unit) capable of detecting three-dimensional information. The three-dimensional measuring equipment may be, for example, a ToF (Time-of-Flight) sensor.

A patient image captured by a camera may cause a color variation due to the illumination conditions and the manufacturing error or deterioration of an image sensor. As described above, a patient image is susceptible to a camera, a display device, and equipment and a communication environment in, for example, compression and decompression during transmission. Moreover, in a patient image, a saturated luminance or a color breakup may occur, so that small tumors may escape detection.

To address the problem, three-dimensional information (depth data) on a patient is acquired by a ToF sensor, and the medical practitioner terminal 12 three-dimensionally displays the face of the patient as a monochrome image based on the three-dimensional information. The three-dimensional information includes, for example, point group data. The point group data is less susceptible to the illumination conditions, the equipment, and the communication environment. Hence, stable information can be provided for a medical practitioner regardless of the illumination conditions, the equipment, and the communication environment, though the three-dimensional information has a lower resolution than a patient image and does not include color information.

Other Modification Examples

For example, the server 13 may generate a medical practice summary, which is a summary of the contents of a medical practice, at the end of the medical practice, and the patient terminal 11 may be allowed to download the medical practice summary.

Moreover, a medical practitioner may be allowed to store, for example, patient images and an action record log, which are acquired during telemedicine, in the patient terminal 11 with the consent of a patient.

4. Others

In the present specification, the processing performed by the computer (CPU) in accordance with the program may not necessarily be performed chronologically in the order described in the flowchart. That is, the processing performed by the computer in accordance with the program also includes processing which is performed individually or in parallel (for example, parallel processing or processing by an object).

The program may be a program processed by one computer (processor) or may be distributed and processed by a plurality of computers. Furthermore, the program may be a program transmitted to a remote computer to be executed.

Moreover, in the present specification, a system means a collection of a plurality of constituent elements (including devices and modules (components)) regardless of whether all the constituent elements are contained in the same casing.

Accordingly, a plurality of devices accommodated in separate casings and connected via a network and one device in which a plurality of modules are accommodated in one casing are all systems.

Embodiments of the present technique are not limited to the above-described embodiment and various modifications can be made within the scope of the present technology without departing from the gist of the present technique.

Furthermore, the present technique may have, for example, a configuration of clouding computing in which a plurality of devices share and process one function together via a network.

In addition, each step described in the above flowchart can be executed by one device or shared by a plurality of devices.

Furthermore, in a case where a plurality of kinds of processing are included in a single step, the plurality of kinds of processing included in the single step may be executed by one device or by a plurality of devices in a shared manner.

The advantageous effects described in the present specification are merely exemplary and are not limited, and other advantageous effects may be achieved.

Note that the present technique may also have the following configurations.

(1) A telemedicine system comprising:
   a first imaging unit that images a patient in a first space;
   an image processing unit that corrects an image of the patient based on imaging conditions in the first space and display conditions in a second space for displaying the image of the patient imaged in the first space; and
   a display unit that displays the corrected image of the patient in the second space.

(2) The telemedicine system according to (1), wherein the imaging conditions include illumination conditions of the first space, and
   the display conditions include illumination conditions of the second space.

(3) The telemedicine system according to (2), wherein the image processing unit estimates a skin color of the patient upon changing from the illumination conditions of the first space to the illumination conditions of the second space, and then the image processing unit corrects the image of the patient with reference to the estimated skin color.

(4) The telemedicine system according to (3), wherein the image processing unit corrects the image of the patient by adjusting a white balance.

(5) The telemedicine system according to any one of (2) to (4), wherein the illumination conditions of the first space and the illumination conditions of the second space include conditions of at least one of a color of illumination light, brightness of illumination light, and the kind of light source.

(6) The telemedicine according to any one of (2) to (5), further comprising: a second imaging unit that images a medical practitioner who provides medical care for the patient in the second space; and
   a condition identification unit that identifies the illumination conditions of the first space based on the image of the patient imaged by the first imaging unit and identifies the illumination conditions of the second space based on an image of the medical practitioner imaged by the second imaging unit.

(7) The telemedicine system according to any one of (1) to (6), wherein
the imaging conditions include conditions of at least one of a configuration and a setting of the first imaging unit, and
the display conditions include conditions of at least one of a configuration and a setting of the display unit.

(8) The telemedicine system according to any one of (1) to (7), wherein the image processing unit is capable of changing at least one of presence or absence of a correction to the image of the patient and intensity of a correction according to a user setting.

(9) The telemedicine system according to any one of (1) to (8), wherein at least the imaging conditions or the display conditions include information on at least one of an attribute of the patient and past medical care information on the patient.

(10) The telemedicine system according to any one of (1) to (9), wherein the image processing unit corrects the image of the patient based on contents of conversation between the patient and the medical practitioner who provides medical care for the patient in the second space.

(11) The telemedicine system according to any one of (1) to (10), further comprising a three-dimensional information detection unit that detects three-dimensional information on the patient in the first space,
wherein the display unit displays the three-dimensional information on the patient.

(12) The telemedicine system according to (1), further comprising a condition identification unit that identifies the imaging conditions and the display conditions.

(13) The telemedicine system according to (1) further comprising:
a first information processing device provided with the first imaging unit;
a second information processing device provided with the display unit; and
a third information processing device that is provided with the image processing unit and is connected to the first information processing device and the second information processing device via a network, wherein
the third information processing device receives the image of the patient from the first information processing device via the network and transmits the corrected image of the patient to the second information processing device.

(14) The telemedicine system according to any one of (1) to (5) and (7) to (13), further comprising:
a first information processing device provided with the first imaging unit; and
a second information processing device that is provided with the display unit and the image processing unit and is connected to the first information processing device via a network, wherein
the second information processing device receives the image of the patient from the first information processing device via the network.

(15) A telemedicine method comprising:
imaging a patient in a first space;
correcting an image of the patient based on imaging conditions in the first space and display conditions in a second space for displaying the image of the patient imaged in the first space; and
displaying the corrected image of the patient in the second space.

(16) An information processing device comprising an image processing unit that corrects an image of a patient based on imaging conditions for imaging the patient in a first space and display conditions in a second space for displaying the image of the patient imaged in the first space.

(17) The information processing device according to (16) further comprising an output control unit that controls display of the corrected image of the patient.

(18) A program for causing a computer to perform processing of correcting an image of a patient based on imaging conditions for imaging the patient in a first space and display conditions in a second space for displaying the image of the patient imaged in the first space.

The advantageous effects described in the present specification are merely exemplary and are not limited, and other advantageous effects may be obtained.

REFERENCE SIGNS LIST

1 Telemedicine system
11 Patient terminal
12 Medical practitioner terminal
13 Server
21 Network
101 CPU
105 Display unit
107 Imaging unit
112 Sensor unit
121 Voice recognition unit
122 Data processing unit
123 Output control unit
201 CPU
205 Display unit
207 Imaging unit
212 Sensor unit
221 Voice recognition unit
222 Data processing unit
223 Output control unit
301 CPU
321 Condition identification unit
322 Image processing unit
323 Data processing unit
324 Communication control unit

The invention claimed is:
1. A telemedicine system, comprising:
a first camera configured to image a patient in a first space;
an image processing circuitry unit that corrects-configured to:
estimate a difference between first illumination conditions of the first space and second illumination conditions of a second space, wherein the first illumination conditions are included in a plurality of imaging conditions of the first space and the second illumination conditions are included in a plurality of display conditions of the second space; and
correct a first image of the patient based on the estimated difference between the first illumination conditions and the second illumination conditions; and
a display device configured to display the corrected first image of the patient in the second space.
2. The telemedicine system according to claim 1, wherein the image processing circuitry is further configured to:

estimate a skin color of the patient based on a change in the first illumination conditions of the first space to the second illumination conditions of the second space, and correct the first image of the patient based on the estimated skin color.

3. The telemedicine system according to claim 2, wherein the image processing circuitry is further configured to correct the first image of the patient based on an adjustment of a white balance.

4. The telemedicine system according to claim 1, wherein the first illumination conditions of the first space include at least one of a color of an illumination light of the first space, a brightness of the illumination light of the first space, and a type of a light source of the first space, and the second illumination conditions include at least one of a color of an illumination light of the second space, a brightness of the illumination light of the second space, and a type of a light source of the second space.

5. The telemedicine system according to claim 1, further comprising:
a second camera configured to image a medical practitioner who provides medical care for the patient in the second space; and
a condition identification circuitry configured to:
identify the first illumination conditions of the first space based on the first image of the patient imaged by the first camera, and
identify the second illumination conditions of the second space based on a second image of the medical practitioner imaged by the second camera.

6. The telemedicine system according to claim 1, wherein the plurality of imaging conditions include at least one of a first configuration of the first camera and a first setting of the first camera, and
the plurality of display conditions include at least one of a second configuration of the display device and a second setting of the display device.

7. The telemedicine system according to claim 1, wherein the image processing circuitry is further configured to change at least one of a presence or an absence of a correction to the first image of the patient based on a user setting, and
the image processing circuitry is further configured to change an intensity of the correction to the first image based on the user setting.

8. The telemedicine system according to claim 1, wherein at least one of the plurality of imaging conditions or the plurality of display conditions include information on at least one of an attribute of the patient and past medical care information on the patient.

9. The telemedicine system according to claim 1, wherein the image processing circuitry is further configured to correct the first image of the patient based on a conversation between the patient and a medical practitioner, wherein
the medical practitioner provides medical care for the patient in the second space.

10. The telemedicine system according to claim 1, further comprising a three-dimensional information detection circuitry configured to detect three-dimensional information on the patient in the first space,
wherein the display device is further configured to display the three-dimensional information on the patient.

11. The telemedicine system according to claim 1, further comprising a condition identification circuitry configured to identify the plurality of imaging conditions and the plurality of display conditions.

12. The telemedicine system according to claim 1, further comprising:
a first information processing device configured to connect with the first camera;
a second information processing device configured to connect with the display device; and
a third information processing device configured to connect with the image processing circuitry,
wherein the third information processing device is further configured to connect to the first information processing device and the second information processing device via a network,
wherein the third information processing device is further configured to receive the first image of the patient from the first information processing device via the network and transmit the corrected first image of the patient to the second information processing device.

13. The telemedicine system according to claim 1, further comprising:
a first information processing device configured to connect with the first camera; and
a second information processing device configured to connect with the display device and the image processing circuitry,
wherein the second information processing device is further configured to connect to the first information processing device via a network, and
wherein the second information processing device is further configured to receive the first image of the patient from the first information processing device via the network.

14. A telemedicine method, comprising:
imaging a patient in a first space;
estimating a difference between first illumination conditions of the first space and second illumination conditions of a second space, wherein the first illumination conditions are included in a plurality of imaging conditions of the first space and the second illumination conditions are included in a plurality of display conditions of the second space;
correcting an image of the patient based on the estimated difference between the first illumination conditions and the second illumination conditions; and
displaying the corrected image of the patient in the second space.

15. An information processing device, comprising:
an image processing circuitry configured to:
estimate a difference between first illumination conditions in a first space and second illumination conditions of a second space, wherein the first illumination conditions are included in a plurality of imaging conditions for imaging a patient in the first space and the second illumination conditions are included in a plurality of display conditions of the second space, and wherein the image of the patient is displayed in the second space; and
correct the image of the patient based the estimated difference between the first illumination conditions and the second illumination conditions.

16. The information processing device according to claim 15, further comprising an output control circuitry configured to display the corrected image of the patient.

17. A non-transitory computer-readable medium having stored thereon, computer-executable instructions which, when executed by a computer, cause the computer to execute operations, the operations comprising:

estimating a difference between first illumination conditions in a first space and second illumination conditions of a second space, wherein the first illumination conditions are included in a plurality of imaging conditions for imaging a patient in the first space and the second illumination conditions are included in a plurality of display conditions of the second space, and wherein the image of the patient is displayed in the second space; and correcting the image of the patient based on the estimated difference between the first illumination conditions and the second illumination conditions.

18. A telemedicine system, comprising:

a first camera configured to image a patient in a first space;

an image processing circuitry configured to correct an image of the patient based on a plurality of imaging conditions in the first space and a plurality of display conditions in a second space for displaying the image of the patient imaged in the first space, wherein at least one of the plurality of imaging conditions or the plurality of display conditions include information on an attribute of the patient and past medical care information on the patient; and a display device configured to display the corrected image of the patient in the second space.

* * * * *